United States Patent
Amineh et al.

(10) Patent No.: US 10,571,242 B2
(45) Date of Patent: Feb. 25, 2020

(54) ELIMINATION OF RESIDUAL MAGNETISM EFFECT IN EDDY CURRENT BASED INSPECTION OF PIPES

(71) Applicant: HALLIBURTON ENERGY SERVICES, INC., Houston, TX (US)

(72) Inventors: Reza Khalaj Amineh, Houston, TX (US); Burkay Donderici, Houston, TX (US); Luis San Martin, Houston, TX (US); Aixa Maria Rivera-Rios, Austin, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 72 days.

(21) Appl. No.: 16/074,412

(22) PCT Filed: Aug. 12, 2016

(86) PCT No.: PCT/US2016/046853
§ 371 (c)(1),
(2) Date: Jul. 31, 2018

(87) PCT Pub. No.: WO2018/031042
PCT Pub. Date: Feb. 15, 2018

(65) Prior Publication Data
US 2019/0033052 A1 Jan. 31, 2019

(51) Int. Cl.
*G01B 7/06* (2006.01)
*E21B 47/09* (2012.01)
(Continued)

(52) U.S. Cl.
CPC ............ *G01B 7/10* (2013.01); *E21B 47/0905* (2013.01); *E21B 47/10* (2013.01); *G01B 21/08* (2013.01); *G01N 27/9046* (2013.01)

(58) Field of Classification Search
CPC ........ G01B 21/00; G01B 21/02; G01B 21/08; G01B 7/00; G01B 7/02; G01B 7/06;
(Continued)

(56) References Cited

U.S. PATENT DOCUMENTS

| 4,292,589 A | 9/1981 | Bonner |
| 4,523,148 A | 6/1985 | Maciejewski |

(Continued)

FOREIGN PATENT DOCUMENTS

WO 2014142796 9/2014

OTHER PUBLICATIONS

Acufia, Irlec Alexandra, et al. "Scanning for downhole corrosion." Oilfield Review 22.1 (2010): 42-50.
(Continued)

*Primary Examiner* — Tung X Nguyen
*Assistant Examiner* — David B Frederiksen
(74) *Attorney, Agent, or Firm* — Locke Lord LLP (57) ABSTRACT

Methods, systems, and computer program products for inspecting a pipe in a well using an eddy-current based pipe inspection tool comprises conveying the pipe inspection tool through the well, obtaining a first voltage measurement at an axial position along the pipe from at least one main receiver. The first voltage measurement includes a residual voltage induced in the at least one main receiver by a residual magnetic field resulting from residual magnetism in the pipe. A second voltage measurement is obtained at said axial position along the pipe from at least one second receiver. The first voltage measurement and the second voltage measurement are processed to obtain a processed measurement representing a difference between the first and second voltage measurements. The processed measurement is substantially free of the residual voltage and may be use to estimate a thickness of the pipe and other pipe characteristics.

20 Claims, 7 Drawing Sheets

(51) Int. Cl.
  *E21B 47/10* (2012.01)
  *G01N 27/90* (2006.01)
  *G01B 21/08* (2006.01)

(58) Field of Classification Search
  CPC ........... G01B 7/10; G01B 7/105; E21B 47/09;
      E21B 47/0905; E21B 47/10; G01N 27/72;
      G01N 27/82; G01N 27/90; G01N
      27/9046; G01V 3/00; G01V 3/18–34
  See application file for complete search history.

(56) References Cited

U.S. PATENT DOCUMENTS

| | | | |
|---|---|---|---|
| 5,043,668 A * | 8/1991 | Vail, III | G01V 3/24 |
| | | | 324/368 |
| 5,955,884 A | 9/1999 | Payton et al. | |
| 6,084,403 A * | 7/2000 | Sinclair | G01B 7/06 |
| | | | 166/255.1 |
| 6,176,323 B1 | 1/2001 | Weirich et al. | |
| 6,211,678 B1 | 4/2001 | Hagiwara | |
| 6,288,548 B1 | 9/2001 | Thompson et al. | |
| 7,327,145 B2 | 2/2008 | Haugland | |
| 8,079,414 B2 | 12/2011 | Smaardyk et al. | |
| 2009/0195244 A1 | 8/2009 | Mouget et al. | |
| 2016/0231281 A1* | 8/2016 | Dingman | B63G 8/001 |
| 2016/0370166 A1* | 12/2016 | Yang | E21B 47/082 |
| 2017/0038493 A1* | 2/2017 | Wu | E21B 47/0905 |

OTHER PUBLICATIONS

Arbuzov, Andrey Alexandrovich, et al. "Memory magnetic imaging defectoscopy." SPE Russian Oil and Gas Exploration and Production Technical Conference and Exhibition. Society of Petroleum Engineers, 2012.

Brill, Thilo Michael, et al. "Electromagnetic casing inspection tool for corrosion evaluation." International Petroleum Technology Conference. International Petroleum Technology Conference, 2011.

Garcia, Javier, et al. "Successful Application of a New Electromagnetic Corrosion Tool for Well Integrity Evaluation in old wells completed with reduced diameter tubular." IPTC 2013: International Petroleum Technology Conference. 2013.

* cited by examiner

ELIMINATION OF RESIDUAL MAGNETISM EFFECT IN EDDY CURRENT BASED INSPECTION OF PIPES

TECHNICAL FIELD

The exemplary embodiments disclosed herein relate generally to techniques for electromagnetic characterization of pipes and particularly to methods and apparatuses for reducing or eliminating the effect of residual magnetism in eddy current-based pipe inspections.

BACKGROUND

In oil and gas wells, it is important to be able to monitor and detect corrosion and related damage to pipes (e.g., casings, tubing, etc.) in the wells. Downhole or in-situ pipe inspection typically involve electromagnetic (EM) inspection tools that are conveyed through the interior of the pipe by wireline, slickline, coiled tubing and similar conveyances. The inspection tools typically induce a voltage on the pipes and log or record the voltage along the length of the pipes to determine pipe thickness and other pipe characteristics. These pipe characteristics may then be used to identify the location of corrosion, metal loss, and other defects along the pipes.

There are generally two categories of EM inspection tools: magnetic flux leakage (MFL) based tools, and eddy current (EC) based tools. In general, inspection tools that are based on magnetic flux leakage are considered more suitable for inspecting a single pipe at a time, while those that are based on eddy current are considered better for simultaneous inspection of multiple pipes.

Eddy current-based tools may further be divided into two categories: frequency-domain tools, and time-domain tools. Frequency-domain eddy current-based tools have a transmitter typically in the form of a coil that is excited by a continuous sinusoidal signal to generate a transient magnetic field in the vicinity of the pipes. This transient magnetic field, called a primary field, induces eddy currents in the pipes that in turn generate secondary magnetic fields. The primary and secondary magnetic fields are then detected by a receiver, also typically in the form of a coil, that measures the voltages induced in the receiver by the magnetic fields. The receiver may be the same as the transmitter or it may be a separate receiver that may be co-located with the transmitter or placed further away on the tool from the transmitter. Pipe thickness and other pipe characteristics may then be determined by processing the induced voltages measured by the receiver using well-known inversion techniques.

In time-domain eddy current-based tools, also called pulsed EC (PEC) tools, the transmitter is excited by a pulse signal. As with frequency-domain tools, the pulse signal generates a transient magnetic field as it transitions from an OFF state to an ON state (or from ON to OFF state). The primary field induces eddy currents in the pipes that in turn generate secondary magnetic fields. The primary and secondary fields induce voltages that are then measured by the receiver and processed to determine pipe thickness and other characteristics of the pipes.

Pipes can sometimes have residual magnetism (i.e., be magnetized) because of prior exposure to magnetic fields. The residual magnetism results in a static and non-uniform residual magnetic field about the pipes that can affect the accuracy of eddy current-based tools. Specifically, the residual magnetic field can induce an undesired residual voltage in the receiver as the tool passes through the pipes. The undesired residual voltage may add to or subtract from the voltage induced by the primary and secondary fields in the receiver, resulting in incorrect receiver measurements. The size of the undesired residual voltage may depend on several factors, including the strength of the residual magnetic field, the velocity at which the coil moves through the field, and the dimensions and number of windings in the receiver. If not properly taken into account, these undesired residual voltages can cause eddy current-based tools to produce spurious results.

Accordingly, a need exists for a way to minimize or eliminate the effect of residual magnetism in eddy current-based inspection tools.

BRIEF DESCRIPTION OF THE DRAWINGS

For a more complete understanding of the exemplary disclosed embodiments, and for further advantages thereof, reference is now made to the following description taken in conjunction with the accompanying drawings wherein.

DESCRIPTION OF EXEMPLARY EMBODIMENTS

The following discussion is presented to enable a person skilled in the art to make and use the exemplary disclosed embodiments. Various modifications will be readily apparent to those skilled in the art, and the general principles described herein may be applied to embodiments and applications other than those detailed below without departing from the spirit and scope of the disclosed embodiments as defined herein. Accordingly, the disclosed embodiments are not intended to be limited to the particular embodiments shown, but are to be accorded the widest scope consistent with the principles and features disclosed herein.

As alluded to above, the embodiments disclosed herein provide an apparatus and method for reducing or eliminating the effect of residual magnetism in eddy current-based pipe inspection tools. The disclosed embodiments contemplate several approaches to account for any residual voltage that may be induced by a residual magnetic field resulting from the residual magnetism. These approaches include, in general, (i) modeling variations in the residual magnetic field using magnetic dipoles to isolate and subtract the residual voltage, (ii) subtracting isolated receiver responses from main receiver responses, (iii) subtracting responses of identical receivers placed at specified distances from a transmitter, (iv) subtracting responses of identical receivers on opposite sides of the transmitter, and (v) subtracting responses of identical receivers to identical transmitters.

Figure 1:
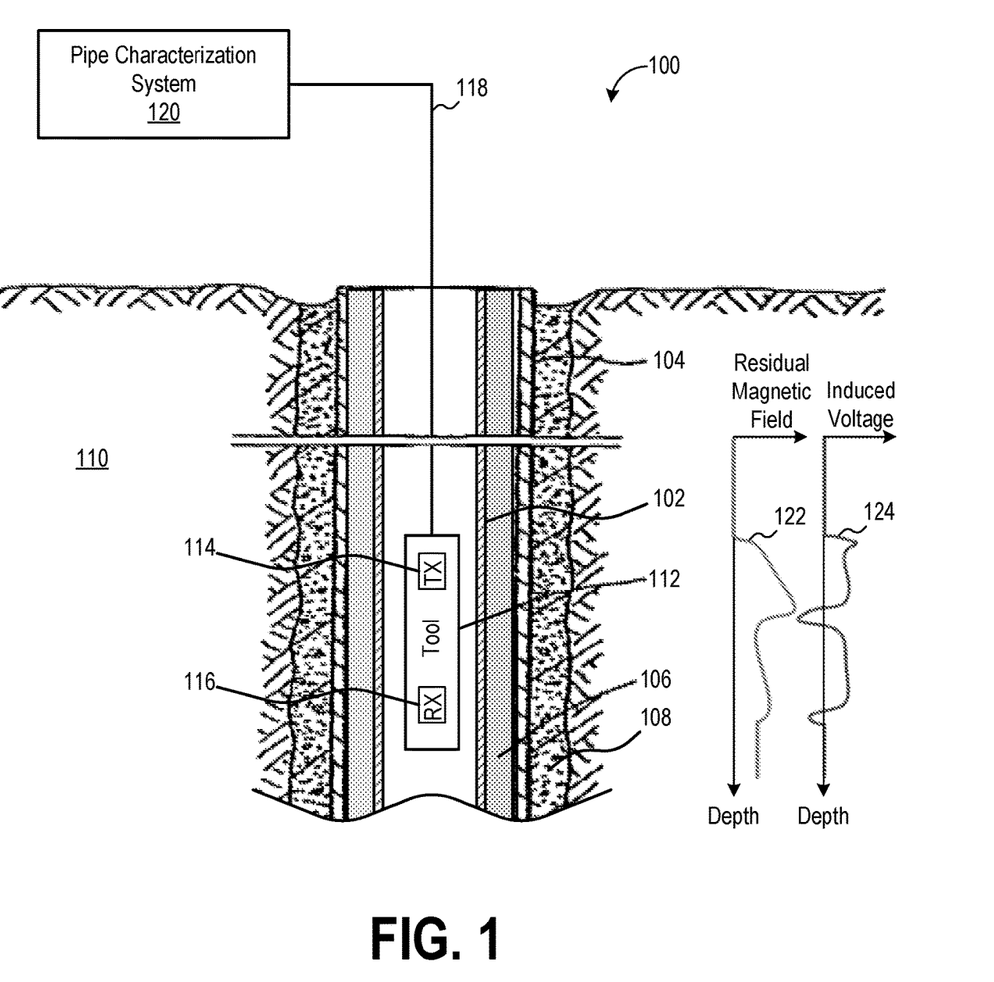
FIG. 1 illustrates an exemplary well in which a pipe inspection tool according to the disclosed embodiments may be used.

Referring now to FIG. 1, a section of an oil or gas well 100 is shown in which one or more of the embodiments disclosed herein may be used to inspect casings, tubing, and other pipes in the well. The particular well 100 depicted may include multiple concentric pipes (e.g., conductor casing, intermediate casing, production casing, etc.), only two of which are shown—an inner pipe 102 and an outer pipe 104. An inner cement sheath 106 fills the annulus between the inner pipe 102 and the outer pipe 104 and an outer cement sheath 108 fills the annulus between the outer pipe 106 and an oil or gas formation 110.

To facilitate inspection of the pipes 102, 104, a pipe inspection tool 112 having one or more transmitters 114 and one or more receivers 116 may be conveyed into the well 100 through the inner pipe 102. Conventional transmitters 114 are contemplated having one or more coils operable to generate a magnetic field from an excitation current in the coils. Likewise, conventional receivers 116 are contemplated having one or more coils operable to measure voltages induced in the coils by a magnetic field. The pipe inspection tool 112 may be an eddy current-based tool in some embodiments, specifically a frequency-domain tool, or the tool 112 may be a time-domain tool in some embodiments. As well, although two pipes 102, 104 are shown, it is possible for the pipe inspection tool 112 to be used to inspect fewer than two pipes 102, 104 at a time or more than two pipes 102, 104 at a time without departing from the scope of the disclosed embodiments.

A wireline 118 conveys the pipe inspection tool 112 through the inner pipe 102. The wireline 118 allows in-situ real-time transmission of data from the tool 112 to a pipe characterization system 120 on the surface of the formation 110. Other conveyances, including slickline, coiled tubing, drill string, downhole tractor, or similar equipment, may also be used to convey the pipe inspection tool 112 through the inner pipe 102. Where slickline and similar equipment is used, data collected by the pipe inspection tool 112 may be stored in the tool 112 and retrieved at a later time for processing.

In general operation, the one or more transmitters 114 generate primary magnetic fields that induce eddy currents in the pipes 102, 104. The eddy currents in turn generate secondary magnetic fields that act on the one or more receivers 116 along with the primary fields. These magnetic fields make up the main magnetic fields for the tool 112 for purposes of pipe inspection and the voltages induced by these fields in the one or more receivers 116 are the main voltages for purposes of pipe inspection. In addition to the main magnetic fields, a residual magnetic field may also be present as a result of residual magnetism on one or more of the pipes 102, 104. The residual magnetic field likewise induces a voltage, albeit undesirable, in the one or more receivers 116. Exemplary plots of the residual magnetic field and the undesirable voltage induced thereby are indicated at 122 and 124, respectively.

The one or more receivers 116 measure the main voltages induced by main magnetic fields and the residual voltage induced by the residual magnetic field and transmit the voltage measurements as data to the pipe characterization system 120. The pipe characterization system 120 thereafter processes the data using inversion techniques to estimate pipe thickness and other pipe characteristics for the pipes 102, 104. Processing of the voltage data may also take place in the pipe inspection tool 112 itself in some embodiments, or a portion of the processing may take place in the pipe inspection tool 112 and a portion in the pipe characterization system 120 in some embodiments. In either case, the presence of the residual voltage may cause the pipe characterization system 120 to produce less accurate characterizations of the pipes 102, 104.

Therefore, in accordance with the disclosed embodiments, the pipe characterization system 120 is designed to account for the residual voltage. To this end, the one or more transmitters 114 and one or more receivers 116 may be arranged on the pipe inspection tool 112 in specific configurations that make it possible or at least easier to account for the residual voltage. This ability to account for the residual voltage allows the pipe characterization system 120 to eliminate or minimize the effect of any residual magnetism on the pipes 102, 104.

Figure 2:
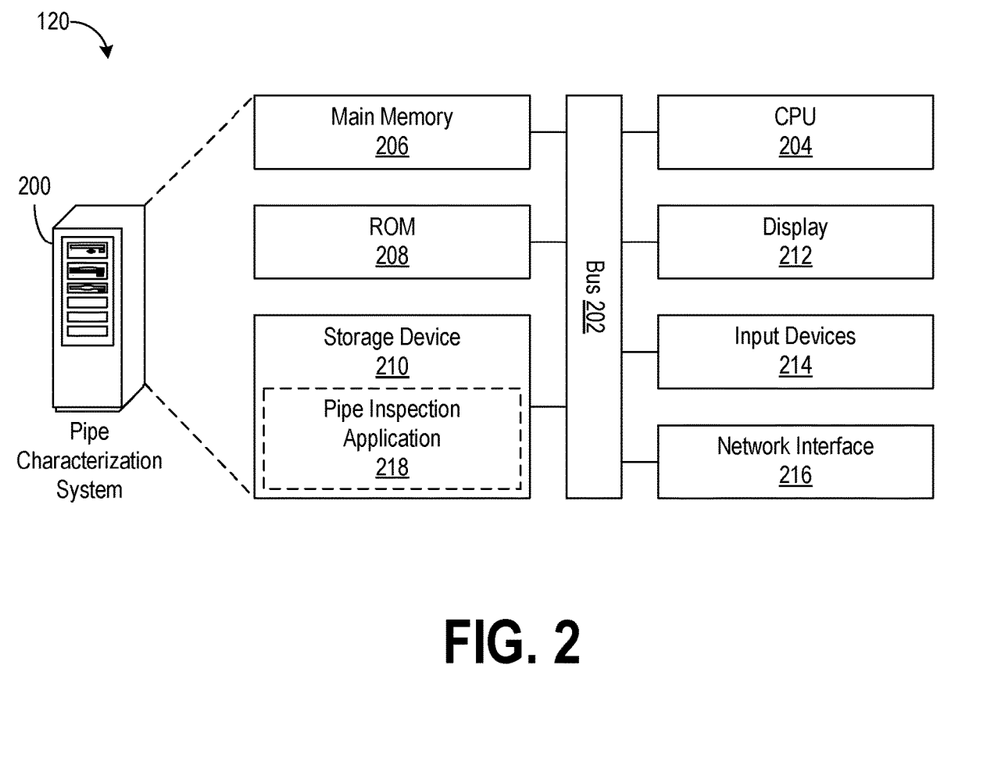
FIG. 2 illustrates an exemplary system that may be used with the pipe inspection tool according to the disclosed embodiments.

FIG. 2 illustrates an exemplary implementation of the pipe characterization system 120 according to the embodiments disclosed herein. In general, the pipe characterization system 120 may include a computing system 200, such as a workstation, desktop, or laptop computer, or it may include a custom computing system developed for a particular application. In a typical arrangement, the computing system 200 includes a bus 202 or other communication pathway for transferring information among other modules within the computing system 200, and a CPU 204 coupled with the bus 202 for processing the information. The computing system 200 may also include a main memory 206, such as a random access memory (RAM) or other dynamic storage device coupled to the bus 202 for storing computer-readable instructions to be executed by the CPU 204. The main memory 206 may also be used for storing temporary variables or other intermediate information during execution of the instructions by the CPU 204.

The computing system 200 may further include a read-only memory (ROM) 208 or other static storage device coupled to the bus 202 for storing static information and instructions for the CPU 204. A computer-readable storage device 210, such as a nonvolatile memory (e.g., Flash memory) drive or magnetic disk, may be coupled to the bus 202 for storing information and instructions for the CPU 204. The CPU 204 may also be coupled via the bus 202 to a display 212 for displaying information to a user. One or more input devices 214, including alphanumeric and other keyboards, mouse, trackball, cursor direction keys, and so forth, may be coupled to the bus 202 for transferring information and command selections to the CPU 204. A communications interface 216 may be provided for allowing the computing system 200 to communicate with an external system or network.

The term "computer-readable instructions" as used above refers to any instructions that may be performed by the CPU 204 and/or other modules. Similarly, the term "computer-readable medium" refers to any storage medium that may be used to store the computer-readable instructions. Such a medium may take many forms, including, but not limited to, non-volatile media, volatile media, and transmission media. Non-volatile media may include, for example, optical or magnetic disks, such as the storage device 210. Volatile media may include dynamic memory, such as main memory 206. Transmission media may include coaxial cables, copper wire and fiber optics, including the wires of the bus 202. Transmission itself may take the form of electromagnetic, acoustic or light waves, such as those generated for radio frequency (RF) and infrared (IR) data communications. Common forms of computer-readable media may include, for example, magnetic medium, optical medium, memory chip, and any other medium from which a computer can read.

A pipe inspection application 218, or the computer-readable instructions therefor, may also reside on or be downloaded to the storage device 210 for execution. In accordance with the disclosed embodiments, the pipe inspection application 218 is capable of eliminating or reducing the effect of any residual magnetism in the pipes 102, 104. The pipe inspection application 218 may be a standalone application or it may be part of a larger suite of software applications that may be used to obtain an overall characterization of the well 100. Such a pipe inspection application 218 may be implemented in any suitable computer programming language or software development package known to those having ordinary skill in the art, including various versions of C, C++, FORTRAN, and the like. Users may then use the pipe inspection application 218 to obtain more accurate estimates of pipe thickness and other pipe characteristics.

Figure 3:
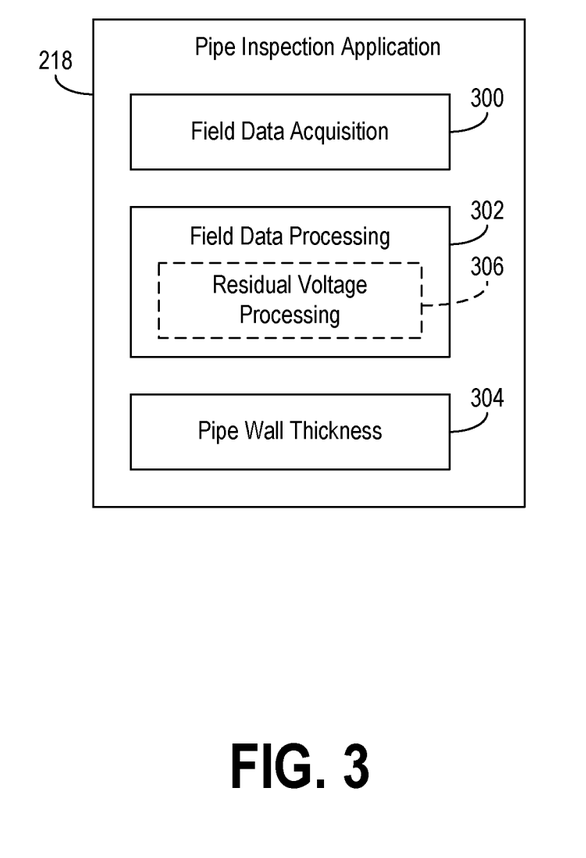
FIG. 3 illustrates an exemplary application that may be used with the pipe inspection tool according to the disclosed embodiments.

An exemplary implementation of the pipe inspection application 218 is depicted in FIG. 3. In this exemplary implementation, the application 218 has been provided with a number of functional modules, including a field data acquisition module 300, a field data processing module 302, and a pipe wall thickness module 304. Other functional modules known to those having ordinary skill in the art may also be provided without departing from the scope of the disclosed embodiments. Note also that although the various modules 300-304 are depicted here as discrete blocks, it should be understood that any block may be divided into two or more constituent blocks and that two or more blocks may be combined to form a single block without departing from the scope of the exemplary disclosed embodiments.

In general operation, the field data acquisition module 300 receives or otherwise obtains data representing voltage measurements from the one or more receivers 116 on the pipe inspection tool 112. These voltage measurements reflect both the main voltages induced by the main magnetic fields and any residual voltage induced by a residual magnetic field. The acquired data is then provided to the field data processing module 302 for processing, which may involve cleaning, converting, storing, and performing inversion on the data, among other processing related tasks known to those skilled in the art. The processed data may then be used by the pipe wall thickness module 304 to estimate wall thickness and other characteristics of the pipes 102, 104. These characteristics may then be displayed graphically, numerically, or both, to allow an operator to analyze and identify areas along the pipes 102, 104 that may be weakened or otherwise defective due to corrosion, metal loss, or related damage.

In accordance with the disclosed embodiments, the field data processing module 302 may include a residual voltage processing module 306 that operates to subtract, cancel, and otherwise account for any residual voltage that may be present due to residual magnetism on the pipes 102, 104. This accounting in turn allows the pipe wall thickness module 304 to provide more accurate estimations of pipe wall thickness and other pipe characteristics. Exemplary implementations of the disclosed embodiments that account for the residual voltage are described below with respect to FIGS. 4-8.

Figure 4:
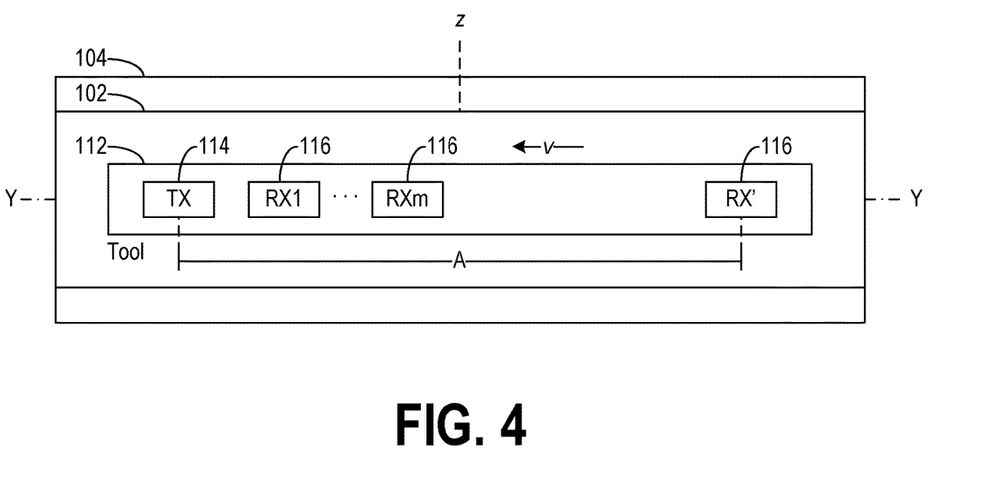
FIG. 4 illustrates an exemplary implementation of the pipe inspection tool according to the disclosed embodiments.

Referring now to FIG. 4, in one embodiment, the residual voltage processing module 306 may account for any residual voltage present by isolating the residual voltage. The isolated residual voltage may then be subtracted from the measurements made by the one or more receivers 116. The subtraction leaves only or mostly the main voltages induced by the main magnetic fields for subsequent use in the pipe wall thickness module 304 to estimate pipe characteristics.

By way of background, it is well known that the induced voltage measured by a receiver due to a residual magnetic field, designated herein as residual voltage $V_r$, may be expressed mathematically as Equation (1) below:

$$V_r(z) = -\frac{d\Phi_r(z)}{dt} \quad (1)$$

In the equation, $\Phi_r$ (phi) is the magnetic flux passing through the receiver and z is an axial position along the length of the pipe (e.g., depth for a vertical section of the well). Letting v denote the velocity at which the receiver moves through the pipe (i.e., logging velocity) allows the residual voltage from Equation (1) to be expressed as Equation (2) below:

$$V_r(z) = -v\frac{d\Phi_r(z)}{dz} \quad (2)$$

In Equation (2), the derivative of $\Phi_r$ with respect to time t has been replaced with the derivative of $\Phi_r$ with respect to axial position z times the receiver velocity v. From this equation, it may be surmised that the residual voltage $V_r$ measured by the receiver due to the residual magnetic field is proportional to the velocity v of the receiver times the derivative of $\Phi_r$ with respect to axial position z.

With the above background filled in, attention is now turned to isolating the residual voltage. To isolate the residual voltage, variations in the strength of the residual magnetic field need to be modeled. As mentioned earlier, residual magnetism typically results in a static, but non-uniform residual magnetic field that varies in field strength along the length of a pipe. These variations in the field strength of the residual magnetic field may be modeled using a magnetic dipole in some embodiments. Specifically, the effect of the residual magnetic field may be modeled as a voltage induced by magnetic dipoles along the pipe, which allows a field strength of the magnetic dipoles along the pipe to be determined. The residual voltage at an axial position along the pipe may then be calculated using the field strength of the magnetic dipole at that axial position. In particular, for a given section of pipe, the magnetic dipole has field strength a(z) where z represents axial positions along the length of the section of pipe (i.e., along line Y-Y in FIG. 4). Estimating the field strength a(z) at axial positions z along the length of the pipe section allows the residual voltage at those axial positions to be estimated. The estimated residual voltages may then be subtracted from the receiver measurements at those axial positions.

To implement the magnetic dipole approach, the pipe inspection tool 112 may be configured with a transmitter 114, a receiver 116 located far from the transmitter 114, and other receivers 116 located near the transmitter 114. The near receivers 116, depicted as main receivers RX1 to RXm, should be close enough to the transmitter 114, depicted as transmitter TX, to have a statistically meaningful (i.e., non-negligible) response to transmitter TX (i.e., to the main magnetic fields resulting from transmitter TX). The far receiver 116, depicted as isolated receiver RX', should be sufficiently separated on the tool 112 from transmitter TX to have no response or a statistically negligible response to transmitter TX (i.e., to the main magnetic fields resulting from transmitter TX). The separation of the transmitter from the isolated receiver RX', indicated by distance "A" in the figure, allows the isolated receiver RX' to measure only or mostly the voltage induced by the residual magnetic field, while the main receivers RX1 to RXm measure the voltages induced by both the main magnetic fields and the residual magnetic field. The distance "A" may depend on several factors, including the dimensions of the tool 112, the strength of the magnetic fields resulting from transmitter TX, and the like, and may be about 80 inches (203 centimeters) or more in some embodiments. In addition (or alternatively), the response of isolated receiver RX' to transmitter TX (i.e., to the main magnetic fields resulting from transmitter TX) should be less than 1 percent of the response of receiver RX' to the residual magnetic field in some embodiments.

With the tool 112 thus configured, the total residual voltage $V_r(z)$ for a given section of pipe may be found by adding the residual voltages measured by the isolated receiver RX' at each axial position z along the section of pipe. The total residual voltage $V_r(z)$ found may then be substituted into Equation (2) to estimate the residual voltage at any main receiver RX1 to RXm. Specifically, by discretizing the residual magnetic field with respect to i in the axial direction, Equation (2) may be expressed as Equation (3) below:

$$\frac{V_r(z)}{v(z)} = -\sum_{i=1}^{N} a(z_i)\frac{d\Phi_r(z-z_i)}{dz} \quad (3)$$

In Equation (3), $\Phi_r$ is the flux produced in any receiver due to a magnetic dipole and may be obtained using well-known techniques, such as by simulation, while the coefficients $a(z_i)$ represent the field strength of the residual magnetic field at axial position $z_i$ (i.e., a magnetic dipole with strength $a(z_i)$). The field strength coefficients $a(z_i)$ for any receiver may then be obtained from the total residual voltage $V_r(z)$ that was found above using known methods of solving systems of equations, such as the least square method.

Once the field strength coefficients $a(z_i)$ are obtained, the residual voltage at any main receiver (i.e., RX1 to RXm) may be approximated by again using Equation (3) along with the receiver velocity v(z) (which is known) and the flux $\Phi_r$ (which may be simulated) for that receiver. This approximation of the residual voltage at any receiver may then be subtracted from the voltage measurement made at that receiver, leaving only or mostly the main voltages that were induced by the main magnetic fields for use in estimating pipe characteristics.

Figure 5:
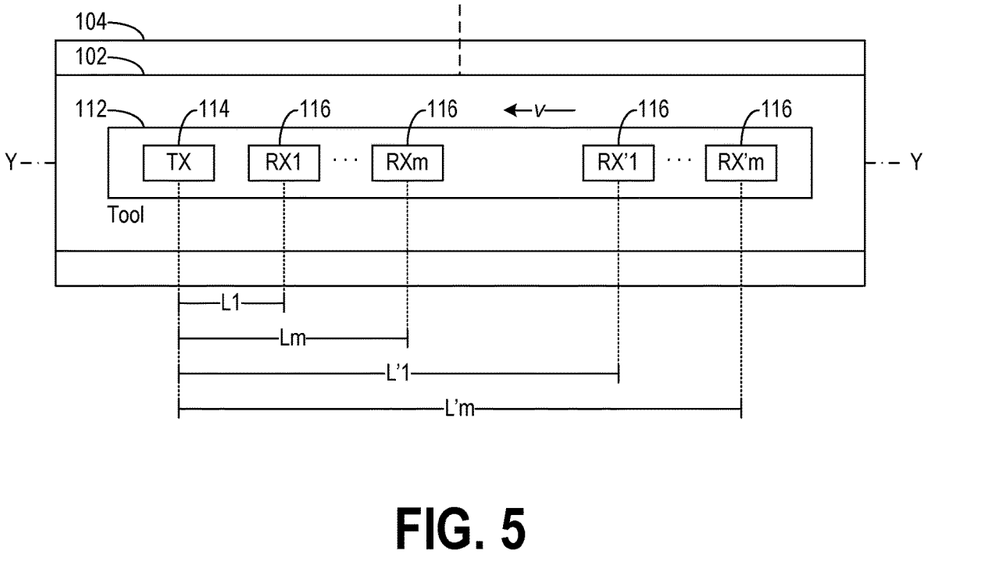
FIG. 5 illustrates another exemplary implementation of the pipe inspection tool according to the disclosed embodiments.

FIG. 5 illustrates another exemplary embodiment where the residual voltage processing module 306 may account for the residual voltage by isolating and subtracting the residual voltage. In this embodiment, the pipe inspection tool 112 may include a set of main receivers RX1 to RXm (116) and a corresponding set of isolated receivers RX'1 to RX'm.

Each of the main receivers RX1 to RXm may be identical or nearly identical to its corresponding isolated receiver RX'1 to RX'm in terms of dimensions, number of windings, and the like. The main receivers RX1 to RXm are again located close enough to the transmitter TX (114) to produce a non-negligible response to transmitter TX (i.e., to the primary and secondary magnetic fields resulting from transmitter TX). The isolated receivers RX'1 to RX'm are again placed sufficiently far from transmitter TX so that they have no response or a negligible response to transmitter TX (i.e., to the primary and secondary magnetic fields resulting from transmitter TX) and measure only or mostly the residual voltages induced by the residual magnetic field. The separation is indicated here by distances L'1 to L'm and may be more than 80 inches (203 centimeters) in some embodiments and/or the responses of isolated receivers RX'1 to RX'm to transmitter TX should be less than 1 percent of their responses to the residual magnetic field in some embodiments.

With the tool 112 thus configured, each isolated receiver RX'1 to RX'm may now directly measure the residual voltage at a given axial position z and provide the measurement to the residual voltage processing module 306 (e.g., via the field data acquisition module 300). The residual voltage processing module 306 may thereafter subtract the residual voltage measurement made by each isolated receiver RX'1 to RX'm from the measurement made by its counterpart main receiver RX1 to RXm at axial position z. Preferably the main receivers RX1 to RXm and the isolated receivers RX'1 to RX'm have their locations on the tool 112 (i.e., L1 to Lm and L'1 to L'm) and their logging velocities aligned or coordinated with one another so that a predefined portion (e.g., the center) of each receiver moves over axial position z with the same or about the same velocity for a given measurement.

Operation of the embodiment of FIG. 5 may be described mathematically as follows. Let $V^{RXi}(z)$ denote the voltage induced at the main receiver RXi, let $V^{RX'i}(z)$ denote the voltage induced at the corresponding isolated receiver RX'i, let $v_0^{RXi}(z)$ denote the velocity of the main receiver RXi when it is centered at z, and let $v_0^{RX'i}(z)$ denote the velocity of the corresponding isolated receiver RX'i when it is centered at z. If the main voltage (i.e., induced by the main magnetic fields and not the residual magnetic field) at receiver RXi is denoted as $V_{pipe}^{RXi}(z)$, then the voltage induced at each main receiver RXi may be expressed as Equation (4) below, and the voltage induced at each isolated receiver RX'i may be expressed as Equation (5) below:

$$V^{RXi}(z) = V_{pipe}^{RXi}(z) - v_0^{RXi}(z)\frac{d\Phi_r(z)}{dz} \quad (4)$$

$$V^{RX'i}(z) = v_0^{RX'i}(z)\frac{d\Phi_r(z)}{dz} \quad (5)$$

As can be seen, Equation (5) reflects only or mostly the residual voltage induced by the residual magnetic field. Therefore, to account for the residual voltage, the residual voltage processing module 306 may multiply Equation (5) by the ratio of the velocity $v_0^{RXi}(z)$ of receiver RXi over the velocity $v_0^{RX'i}(z)$ of receiver RX'i and subtract the result from Equation (4), as shown in Equation (6) below:

$$V^{processed}(z) = V^{RXi}(z) - \frac{v_0^{RXi}}{v_0^{RX'i}(z)}V^{RX'i}(z) \quad (6)$$

In Equation (6), $V^{processed}(Z)$ denotes a voltage that is now free or substantially (i.e., more than 90 percent) free of any residual voltage for purposes of estimating pipe characteristics.

Figure 6:
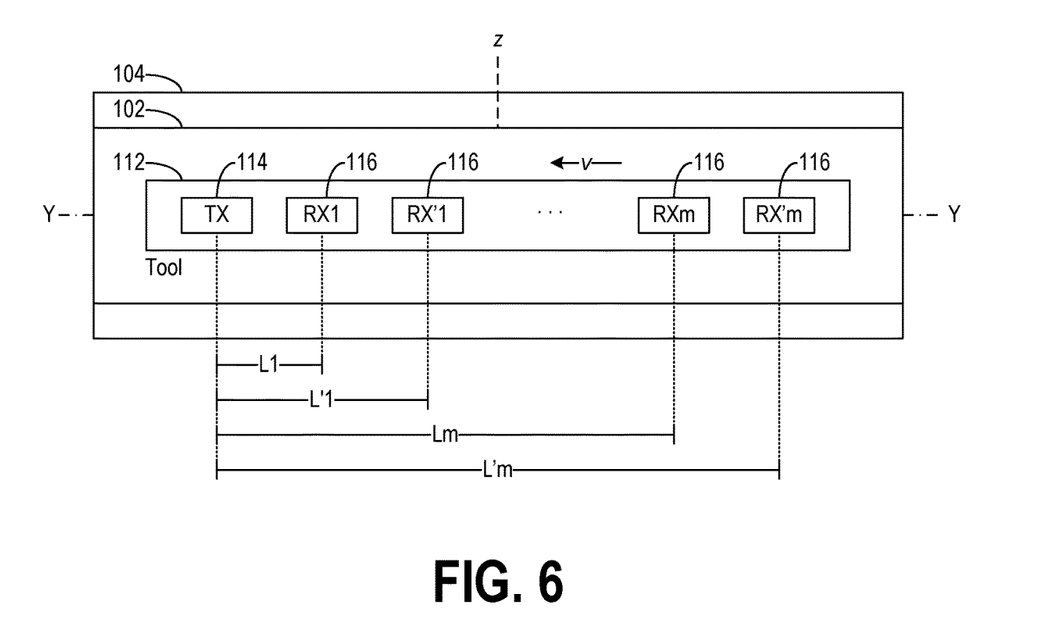
FIG. 6 illustrates yet another exemplary implementation of the pipe inspection tool according to the disclosed embodiments.

FIG. 6 illustrates another exemplary embodiment where the residual voltage processing module 306 may account for any residual voltage that may be present due to residual magnetism. In this embodiment, the residual voltage processing module 306 uses a differential response of a receiver pair to account for any residual voltage. The embodiment contemplates a configuration of the pipe inspection tool 112 that uses pairs of receivers (116). For example, receivers RX1 and RX'1 form one receiver pair, receivers RXm and RX'm form another pair, and so forth. The receivers RX1 and RX'1, RXm and RX'm making up each receiver pair need not be adjacent to one another, but should be identical or nearly identical to one another (i.e., RX1 is identical or nearly identical to RX'1, RXm is identical or nearly identical to RX'm, etc.). This allows one receiver to measure the same or nearly the same amount of residual voltage as the other receiver in a receiver pair at a given axial position z. Thus, by aligning or coordinating their positions on the tool 112 (i.e., by coordinating L1, L'1, Lm, and L'm) and their velocities with respect to axial position z, the responses of these identical or nearly identical receivers may be subtracted to account for the residual voltage.

Operation of the embodiment of FIG. 6 may be described mathematically as follows. Let $V^{RXi}(z)$ denote the voltage induced at one receiver RXi in the pair of receivers, let $V^{RX'i}(z)$ denote the voltage induced at the other receiver RX'i in the pair of receivers, let $v_0^{RXi}(z)$ denote the velocity of receiver RXi when it is centered at z, and let $v_0^{RX'i}(z)$ denote the velocity of the other receiver RX'i when it is centered at z. If the main voltage induced at receiver RXi is denoted as $V_{pipe}^{RXi}(z)$, and the main voltage induced at receiver RX'i is denoted as $V_{pipe}^{RX'i}(z)$, then the voltage induced at RXi may be expressed as Equation (7) below, and the voltage induced at RX'i may be expressed as Equation (8) below:

$$V^{RXi}(z) = V_{pipe}^{RXi}(z) - v_0^{RXi}(z)\frac{d\Phi_r(z)}{dz} \quad (7)$$

$$V^{RX'i}(z) = V_{pipe}^{RX'i}(z) - v_0^{RX'i}(z)\frac{d\Phi_r(z)}{dz} \quad (8)$$

To account for the residual voltage, the residual voltage processing module 306 may multiply Equation (8) by the ratio of the velocity $v_0^{RXi}(z)$ of receiver RXi over the velocity $v_0^{RX'i}(z)$ of receiver RX'i and subtract the result from Equation (7), as shown in Equation (9) below:

$$V^{processed}(z) = V^{RXi}(z) - \frac{v_0^{RXi}(z)}{v_0^{RX'i}(z)} V^{RX'i}(z) \quad (9)$$

$$= V_{pipe}^{RXi}(z) - \frac{v_0^{RXi}(z)}{v_0^{RX'i}(z)} V_{pipe}^{RX'i}(z)$$

In Equation (9), $V^{processed}(z)$ again denotes a voltage that is now free or substantially (i.e., more than 90 percent) free of any residual voltage for purposes of estimating pipe characteristics. In some embodiments, if the receivers in the receiver pairs are not identical, correction coefficients may be derived and applied to the receiver measurements to compensate for the difference in a manner known to those skilled in the art before performing the subtraction described above. Note also that an inversion process that is specific to differential responses should be employed for the differential responses (i.e., the inputs to the inversion process are differential responses).

Figure 7:
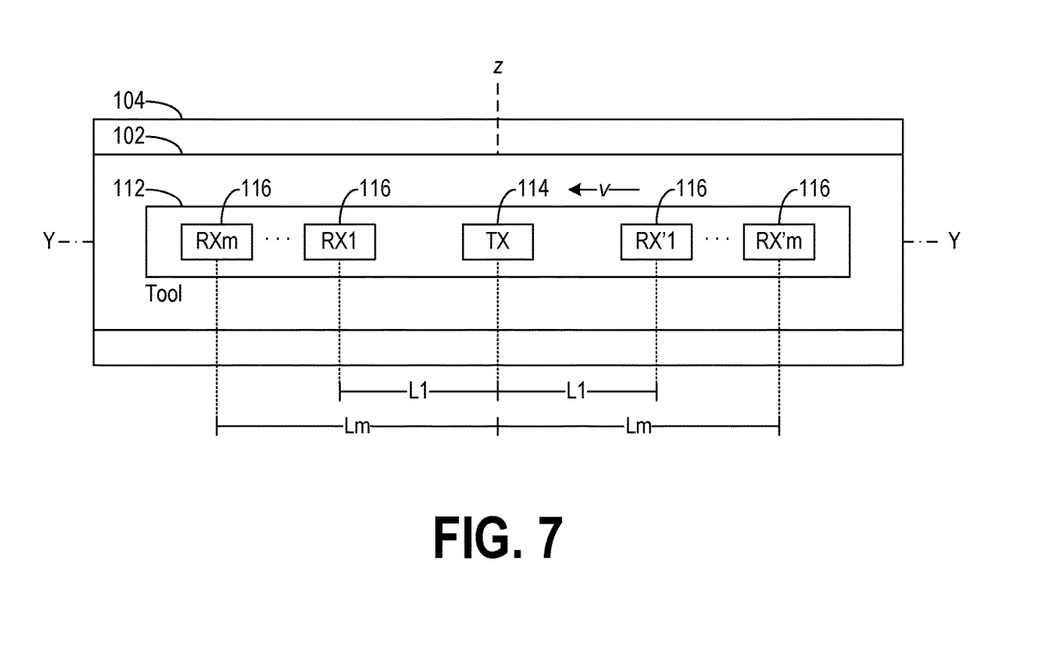
FIG. 7 illustrates still another exemplary implementation of the pipe inspection tool according to the disclosed embodiments.

FIG. 7 illustrates yet another exemplary embodiment where the residual voltage processing module 306 may account for any residual voltage that may be present due to residual magnetism. In this embodiment, the residual voltage processing module 306 again uses differential responses of identical or nearly identical receivers on the pipe inspection tool 112. Specifically, the identical or nearly identical receivers (116) are placed on the tool 112 at identical or nearly identical distances from the transmitter (114), but on opposite sides of the transmitter. This configuration results in spaced apart pairs of receivers on the tool 112, each pair composed of a receiver on one side and a second receiver on the other side of the transmitter, the two receivers being equidistance from the one or more transmitters 114. For example, receivers RX1 and RX'1 form one receiver pair, receivers RXm and RX'm form another receiver pair, and so forth, with each receiver and its counterpart being on opposite sides of transmitter TX.

When thus configured, voltages induced at each receiver in a given receiver pair by the main magnetic fields (i.e., main voltages) at axial position z have substantially the same (i.e., more than 90 percent) magnitude, but opposite phases, assuming substantially the same windings and voltage measurement directions. On the other hand, voltages induced at each receiver in the given receiver pair by the residual magnetic field (i.e., residual voltages) at the same axial position z have substantially the same magnitude and phases. Thus, by aligning or coordinating the positions of the receivers on the tool 112 (i.e., by coordinating L1, L'1, Lm, and L'm) and their velocities with respect to axial position z, then subtracting the measurements of the two receivers in the receiver pair, the residual voltage can be removed.

Operation of the embodiment of FIG. 7 may be described mathematically as follows, using the same variable notations as from the previous equations:

$$V^{RXi}(z) = V_{pipe}^{RXi}(z) - v_0^{RXi}(z)\frac{d\Phi_r(z)}{dz} \quad (10)$$

$$V^{RX'i}(z) = V_{pipe}^{RX'i}(z) - v_0^{RX'i}(z)\frac{d\Phi_r(z)}{dz} \quad (11)$$

$$\approx -V_{pipe}^{RXi}(z) - v_0^{RX'i}(z)\frac{d\Phi_r(z)}{dz}$$

Once again, to account for the residual voltage, the residual voltage processing module 306 may multiply Equation (11) by the ratio of the velocity $v_0^{RXi}(z)$ of receiver RXi over the velocity $v_0^{RX'i}(z)$ of receiver RX'i and subtract the result from Equation (10), as shown in Equation (12) below:

$$V^{processed}(z) = V^{RXi}(z) - \frac{v_0^{RXi}(z)}{v_0^{RX'i}(z)} V^{RX'i}(z) \quad (12)$$

$$= V_{pipe}^{RXi}(z) - \frac{v_0^{RXi}(z)}{v_0^{RX'i}(z)} V_{pipe}^{RX'i}(z)$$

where $V^{processed}(z)$ again denotes a voltage that is now free or substantially free of any residual voltage for purposes of estimating pipe characteristics. As before, if the receivers in a receiver pair are not identical, proper correction coefficients may be applied to the measurements made by the receivers before performing the subtraction. Additionally, for characterization of defects regions, the corrected responses need to be processed with an inversion process that is specifically devised for such corrected measurements in a manner known to those skilled in the art (i.e., the inputs to the inversion process are differential responses).

An advantage of the embodiment of FIG. 7 is the ability to use conventional inversion processes as opposed to inversion processes specifically devised for differential responses. For example, for pipe thickness estimations of large defect areas where the axial length of the defect region is much larger than the distance between the two receiver pairs, the differential responses for the pair of receivers are two times the responses of a single receiver, but with the residual voltage induced by the residual magnetic field having been removed. The larger axial length of the defect region thus allows for the use of a conventional inversion process designed for individual receiver responses instead of differential receiver responses.

Figure 8:
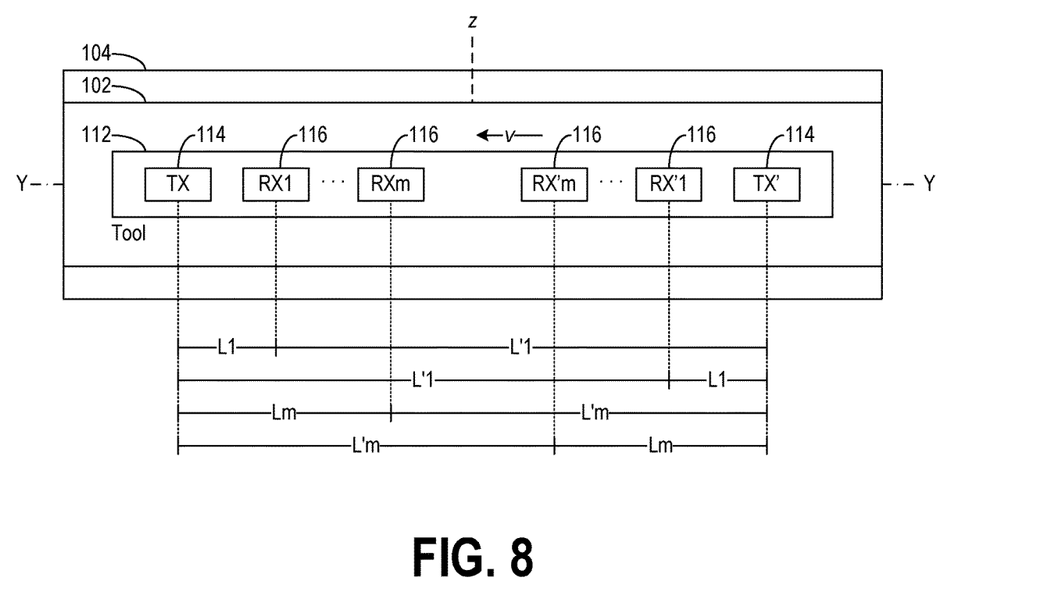
FIG. 8 illustrates yet another exemplary implementation of the pipe inspection tool according to the disclosed embodiments.

FIG. 8 illustrates still another exemplary embodiment where the residual voltage processing module 306 may account for residual voltage due to residual magnetism. In this embodiment, the residual voltage processing module 306 again uses differential responses of identical or nearly identical receivers (116), but with two identical or nearly identical transmitters (114). As can be seen, two transmitters TX and TX' are deployed on opposite sides of two groups of receivers, with transmitter TX being adjacent to receivers RX1 to RXm and transmitter TX' being adjacent to receivers RX'1 to RX'm. Each receiver in one group (e.g., RX1 to RXm) is identical to or nearly identical to its corresponding receiver in the other group (e.g., RX'1 to RX'm) and is positioned on the pipe inspection tool 112 the same or about the same distance from the transmitter TX or TX' for that group, respectively. For example, the distance from receiver RX1 to transmitter TX1 and the distance from receiver RX'1 to transmitter TX'1 is L1, whereas the distance from receiver RX1 to transmitter TX'1 and the distance from receiver RX'1 to transmitter TX1 is L'1.

When thus configured, the main voltages induced in receivers RX1 and RX'1 due to the main magnetic fields from transmitter TX and TX', respectively, are the same or similar in magnitude at axial position z, but opposite in phases (assuming again substantially the same windings and voltage measurement directions). On the other hand, because the receivers are identical or nearly identical, they measure the same or nearly the same residual voltage (magnitude and phase) induced by any residual magnetic field. Thus, by aligning or coordinating the positions of the receivers on the tool 112 (i.e., by coordinating L1, L'1, Lm, and L'm) and their velocities with respect to axial position z and subtracting the voltage measurements of the receivers in each receiver pair, the residual voltage can be removed.

Operation of the embodiment of FIG. 8 may be described mathematically using the same Equations (10)-(12) and variable notations as in the embodiment of FIG. 7 and thus is not repeated here for economy of the description. Similarly, if the two receivers are not identical, proper correction coefficients may be applied to the responses before making the subtraction. For characterization of smaller defect regions, the corrected responses should be processed with an inversion process that is devised for such responses (i.e., the inputs of the inversion are differential responses). This embodiment likewise has an advantage in that, for larger axial length defect regions, the embodiment allows the use of a conventional inversion process designed for individual receiver responses and instead of differential receiver responses.

Figure 9:
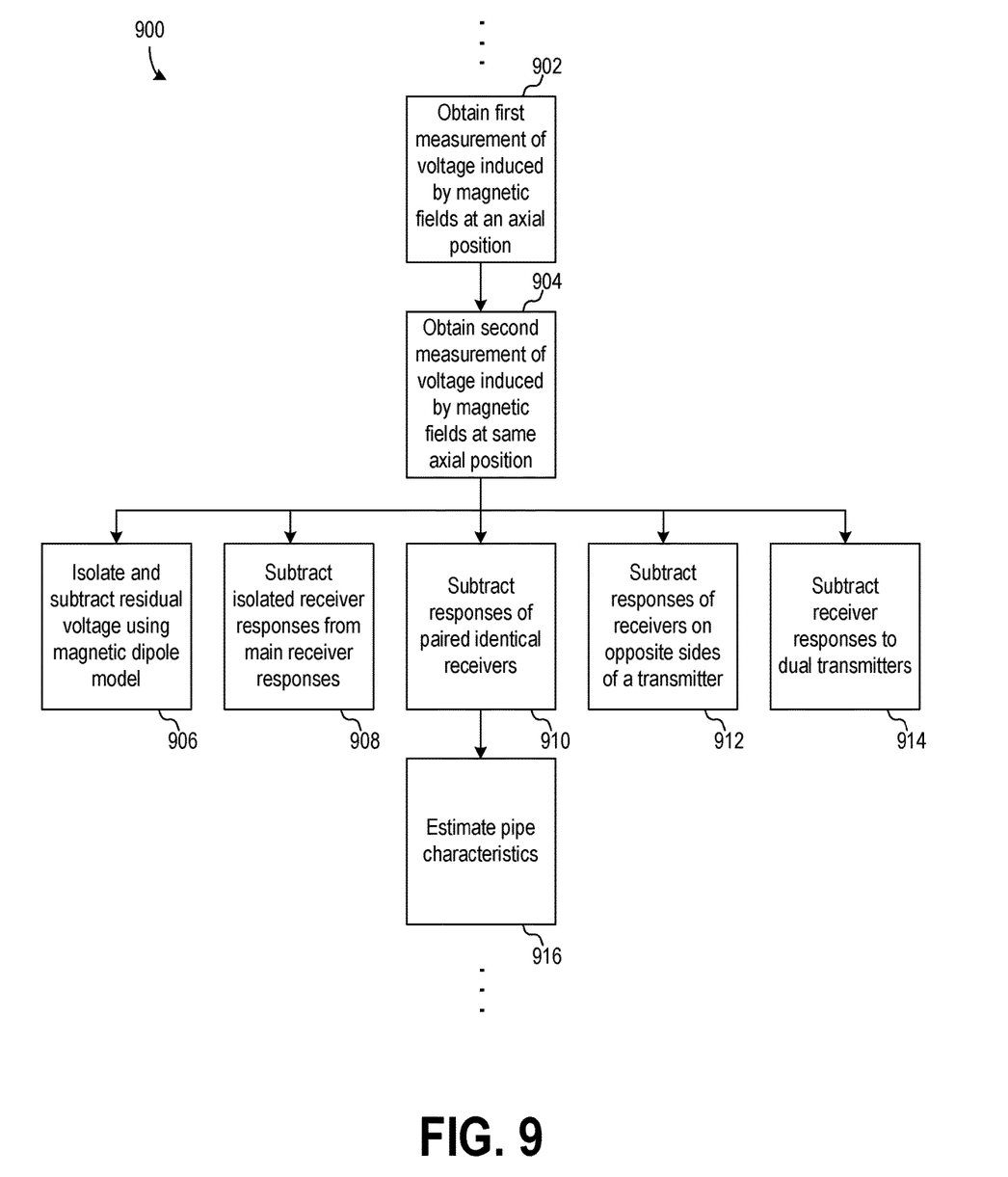
FIG. 9 illustrates an exemplary workflow that may be used with the pipe inspection tool according to the disclosed embodiments.

Thus far, a number of specific embodiments have been described for accounting for the residual voltage induced by a residual magnetic field. Following now in FIG. 9 are general guidelines in the form of a flow chart 900, or portion thereof, outlining a method that may be used to account for the residual voltage. Those having ordinary skill in the art will understand of course that alternative arrangements may be derived from the teachings presented herein without departing from the scope of the disclosed embodiments.

As can be seen in FIG. 9, the workflow 900, or portion thereof, begins at block 902 where data representing a first measurement of voltage induced by magnetic fields is obtained by a first (i.e., RX1 to RXm) receiver at an axial position on a pipe. The measurement typically includes main voltages induced by main magnetic fields as well as any residual voltage induced by a residual magnetic field. At block 904, data representing a second measurement of voltage induced by magnetic fields is obtained by a second receiver (i.e., RX'1 to RX'm) at the axial position.

The workflow 900 thereafter continues by accounting for the residual voltage using one or more of the approaches described herein. In general, in some embodiments the residual voltage may be accounted for by isolating and subtracting the residual voltage using a magnetic dipole model, as shown at block 906. In general, in some embodiments, the residual voltage may also be accounted for by subtracting isolated receivers responses from main receiver responses, as shown at block 908. In general, in some embodiments, the residual voltage may also be accounted for by subtracting the responses of paired identical receivers, as shown at block 910. In general, in some embodiments, the residual voltage may also be accounted for by subtracting the responses of identical receivers located on opposite sides of a transmitter, as shown at block 912. In general, in some embodiments, the residual voltage may also be accounted for by subtracting the responses of identical receivers to dual identical transmitters, as shown at block 914.

Thereafter, the processed data is used to estimate pipe wall thicknesses and other pipe characteristics at block 916.

Accordingly, as set forth above, the embodiments disclosed herein may be implemented in a number of ways. For example, in general, in one aspect, the disclosed embodiments relate to a method of inspecting a pipe in a well using an eddy-current based pipe inspection tool. The method may comprise, among other things, conveying the pipe inspection tool through the well, the pipe inspection tool having a transmitter (TX), at least one main receiver (RX1 to RXm), and at least one second receiver (RX'1 to RX'm) mounted on the pipe inspection tool. The method may also comprise obtaining a first voltage measurement at an axial position along the pipe from the at least one main receiver (RX1 to RXm), the first voltage measurement comprising a residual voltage induced in the at least one main receiver (RX1 to RXm) by a residual magnetic field resulting from residual magnetism in the pipe. The method may further comprise obtaining a second voltage measurement at said axial position along the pipe from the at least one second receiver (RX'1 to RX'm) and processing the first voltage measurement and the second voltage measurement. A processed measurement is obtained representing a difference between the first and second voltage measurements, the processed measurement being substantially free of the residual voltage. A thickness of the pipe may then be estimated using the processed measurement.

In general, in another aspect, the disclosed embodiments relate to an eddy-current based pipe inspection tool for inspecting a pipe in a well. The pipe inspection tool may comprise, among other things, a transmitter (TX) mounted on the pipe inspection tool, the transmitter (TX) operable to generate a primary magnetic field. The pipe inspection tool may also comprise at least one main receiver (RX1 to RXm) mounted on the pipe inspection tool, each main receiver (RX1 to RXm) operable to provide a first voltage measurement at an axial position comprising a residual voltage induced in the at least one main receiver (RX1 to RXm) by a residual magnetic field resulting from residual magnetism in the pipe. The pipe inspection tool may further comprise at least one second receiver (RX'1 to RX'm) mounted on the pipe inspection tool, each second receiver (RX'1 to RX'm) operable to provide a second voltage measurement at said axial position. The at least one second receiver (RX'1 to RX'm) is positioned on the pipe inspection tool relative to the transmitter (TX) in a manner that allows the residual voltage to be subtracted from the first voltage measurement.

In general, in yet another aspect, the disclosed embodiments relate to a computer-readable medium storing computer-readable instructions for inspecting a pipe in a well using an eddy-current based pipe inspection tool, the pipe inspection tool having a transmitter, at least one main receiver, and at least one second receiver mounted on the pipe inspection tool. The computer-readable instructions cause a computing system to, among other things, convey the pipe inspection tool through the well, the pipe inspection tool having a transmitter (TX), at least one main receiver (RX1 to RXm), and at least one second receiver (RX'1 to RX'm) mounted on the pipe inspection tool. The computer-readable instructions also cause the computing system to obtain a first voltage measurement from the at least one main receiver (RX1 to RXm) taken at an axial position along the pipe, the first voltage measurement comprising a residual voltage induced in the at least one main receiver (RX1 to RXm) by a residual magnetic field resulting from residual magnetism in the pipe. The computer-readable instructions further cause the computing system to obtain a second voltage measurement from the at least one second receiver (RX'1 to RX'm) taken at said axial position along the pipe. The first voltage measurement and the second voltage measurement our processed to obtain a processed measurement representing a difference between the first and second voltage measurements, the processed measurement being substantially free of the residual voltage. A thickness of the pipe may then be estimated using the processed measurement.

In accordance with any one or more of the foregoing embodiments, the at least one second receiver (RX'1 to RX'm) comprises an isolated receiver (RX') located sufficiently far on the pipe inspection tool from the transmitter (TX) so that the isolated receiver (RX') has a negligible response to the transmitter (TX), further comprising modeling the effect of the residual magnetic field as a voltage induced by magnetic dipoles along the pipe, determining a field strength of the magnetic dipoles along the pipe, and calculating the residual voltage at the axial position using the field strength of the magnetic dipoles at the axial position.

In accordance with any one or more of the foregoing embodiments, the at least one second receiver (RX'1 to RX'm) comprises a nearly identical receiver to each one of the at least one main receiver (RX1 to RXm), each one of the at least one main receiver (RX1 to RXm) and the nearly identical receiver (RX'1 to RX'm) corresponding thereto forming a pair of receivers (RX1 and RX'1, RXm and RX'm), each one of the at least one second receivers (RX'1 to RX'm) being located sufficiently far on the pipe inspection tool from the transmitter (TX) so that the at least one second receivers (RX'1 to RX'm) have a negligible response to the transmitter (TX), the processing comprising multiplying the second voltage measurement by a ratio of a velocity of the at least one main receiver over a velocity of the at least one second receiver at the axial position and subtracting the result from the first voltage measurement.

In accordance with any one or more of the foregoing embodiments, the at least one second receiver (RX'1 to RX'm) comprises a nearly identical receiver (RX'1 to RX'm) to each one of the at least one main receiver (RX1 to RXm), each one of the at least one main receiver (RX1 to RXm) and the nearly identical receiver (RX1 to RXm) corresponding thereto forming a pair of receivers (RX1 and RX'1, RXm and RX'm), each main receiver (RX'1 to RX'm) in each pair of receivers (RX1 and RX'1, RXm and RX'm) being located on the same side of the transmitter (TX) as the nearly identical receiver (RX1 to RXm) corresponding thereto, the processing comprising multiplying the second voltage measurement by a ratio of a velocity of the at least one main receiver over a velocity of the at least one second receiver at the axial position and subtracting the result from the first voltage measurement.

In accordance with any one or more of the foregoing embodiments, the at least one second receiver (RX'1 to RX'm) comprises a nearly identical receiver (RX'1 to RX'm) to each one of the at least one main receiver (RX1 to RXm), each one of the at least one main receiver (RX1 to RXm) and the nearly identical receiver (RX1 to RXm) corresponding thereto forming a pair of receivers (RX1 and RX'1, RXm and RX'm), each main receiver (RX'1 to RX'm) in each pair of receivers (RX1 and RX'1, RXm and RX'm) being located equidistance from and on opposite sides of the transmitter (TX) from the nearly identical receiver (RX'1 to RX'm) corresponding thereto, the processing comprising multiplying the second voltage measurement by a ratio of a velocity of the at least one main receiver over a velocity of the at least one second receiver at the axial position and subtracting the result from the first voltage measurement.

In accordance with any one or more of the foregoing embodiments, the transmitter (TX) is a first transmitter (TX), further comprising a second transmitter (TX') nearly identical to the first transmitter (TX) on the pipe inspection tool, the first transmitter (TX) being adjacent to the at least one main receiver (RX1 to RXm) and the second transmitter (TX') being adjacent to the at least one second receiver (RX'1 to RX'm), each one of the at least one main receiver (RX1 to RXm) being nearly identical to one of the at least one second receiver (RX'1 to RX'm), the processing multiplying the second voltage measurement by a ratio of a velocity of the at least one main receiver over a velocity of the at least one second receiver at the axial position and subtracting the result from the first voltage measurement.

In accordance with any one or more of the foregoing embodiments, the first voltage measurement further comprises a main voltage induced in the main receiver (RX1 to RXm) by a primary magnetic field generated by the transmitter (TX) and a secondary magnetic field resulting from eddy currents in the pipe.

While the invention has been described with reference to one or more particular embodiments, those skilled in the art will recognize that many changes may be made thereto without departing from the spirit and scope of the description. Each of these embodiments and obvious variations thereof is contemplated as falling within the spirit and scope of the claimed invention, which is set forth in the following claims.

What is claimed is:

1. A method of inspecting a pipe in a well using an eddy-current based pipe inspection tool, comprising:
   conveying the pipe inspection tool through the well, the pipe inspection tool having a transmitter, at least one main receiver, and at least one second receiver mounted on the pipe inspection tool;
   obtaining a first voltage measurement at an axial position along the pipe from the at least one main receiver, the first voltage measurement comprising a residual voltage induced in the at least one main receiver by a residual magnetic field resulting from residual magnetism in the pipe;
   obtaining a second voltage measurement at said axial position along the pipe from the at least one second receiver;
   processing the first voltage measurement and the second voltage measurement to obtain a processed measurement representing a difference between the first and second voltage measurements, the processed measurement being substantially free of the residual voltage; and
   estimating a thickness of the pipe using the processed measurement.

2. The method of claim 1, wherein the at least one second receiver comprises an isolated receiver located sufficiently far on the pipe inspection tool from the transmitter so that the isolated receiver has a negligible response to the transmitter, further comprising modeling the effect of the residual magnetic field as a voltage induced by magnetic dipoles along the pipe, determining a field strength of the magnetic dipoles along the pipe, and calculating the residual voltage at the axial position using the field strength of the magnetic dipoles at the axial position.

3. The method of claim 1, wherein the at least one second receiver comprises a nearly identical receiver to each one of the at least one main receiver, each one of the at least one main receiver and the nearly identical receiver corresponding thereto forming a pair of receivers, each one of the at least one second receivers being located sufficiently far on the pipe inspection tool from the transmitter so that the at least one second receivers have a negligible response to the transmitter, the processing comprising multiplying the second voltage measurement by a ratio of a velocity of the at least one main receiver over a velocity of the at least one second receiver at the axial position and subtracting the result from the first voltage measurement.

4. The method of claim 1, wherein the at least one second receiver comprises a nearly identical receiver to each one of the at least one main receiver, each one of the at least one main receiver and the nearly identical receiver corresponding thereto forming a pair of receivers, each main receiver in each pair of receivers being located on the same side of the transmitter as the nearly identical receiver corresponding thereto, the processing comprising multiplying the second voltage measurement by a ratio of a velocity of the at least one main receiver over a velocity of the at least one second receiver at the axial position and subtracting the result from the first voltage measurement.

5. The method of claim 1, wherein the at least one second receiver comprises a nearly identical receiver to each one of the at least one main receiver, each one of the at least one main receiver and the nearly identical receiver corresponding thereto forming a pair of receivers, each main receiver in each pair of receivers being located equidistance from and on opposite sides of the transmitter from the nearly identical receiver corresponding thereto, the processing comprising multiplying the second voltage measurement by a ratio of a velocity of the at least one main receiver over a velocity of the at least one second receiver at the axial position and subtracting the result from the first voltage measurement.

6. The method of claim 1, wherein the transmitter is a first transmitter, further comprising a second transmitter nearly identical to the first transmitter on the pipe inspection tool, the first transmitter being adjacent to the at least one main receiver and the second transmitter being adjacent to the at least one second receiver, each one of the at least one main receiver being nearly identical to one of the at least one second receiver, the processing multiplying the second voltage measurement by a ratio of a velocity of the at least one main receiver over a velocity of the at least one second receiver at the axial position and subtracting the result from the first voltage measurement.

7. The method of claim 1, wherein the first voltage measurement further comprises a main voltage induced in the main receiver by a primary magnetic field generated by the transmitter and a secondary magnetic field resulting from eddy currents in the pipe.

8. An eddy-current based pipe inspection tool for inspecting a pipe in a well, comprising:
   a transmitter mounted on the pipe inspection tool, the transmitter operable to generate a primary magnetic field;
   at least one main receiver mounted on the pipe inspection tool, each main receiver operable to provide a first voltage measurement at an axial position comprising a residual voltage induced in the at least one main receiver by a residual magnetic field resulting from residual magnetism in the pipe; and
   at least one second receiver mounted on the pipe inspection tool, each second receiver operable to provide a second voltage measurement at said axial position;
   wherein the at least one second receiver is positioned on the pipe inspection tool relative to the transmitter in a manner that allows the residual voltage to be subtracted from the first voltage measurement.

9. The pipe inspection tool of claim 8, wherein the at least one second receiver comprises an isolated receiver located sufficiently far on the pipe inspection tool from the transmitter so that the isolated receiver has a negligible response to the transmitter.

10. The pipe inspection tool of claim 8, wherein the at least one second receiver comprises a nearly identical receiver to each one of the at least one main receiver, each one of the at least one main receiver and the nearly identical receiver corresponding thereto forming a pair of receivers, each nearly identical receiver being located sufficiently far on the pipe inspection tool from the transmitter so that the nearly identical receivers have a negligible response to the transmitter.

11. The pipe inspection tool of claim 8, wherein the at least one second receiver comprises a nearly identical receiver to each one of the at least one main receiver, each one of the at least one main receiver and the nearly identical receiver corresponding thereto forming a pair of receivers, each main receiver in each pair of receivers being located on the same side of the transmitter as the nearly identical receiver corresponding thereto.

12. The pipe inspection tool of claim 8, wherein the at least one second receiver comprises a nearly identical receiver to each one of the at least one main receiver, each one of the at least one main receiver and the nearly identical receiver corresponding thereto forming a pair of receivers, each main receiver in each pair of receivers being located equidistance from and on opposite sides of the transmitter from the nearly identical receiver corresponding thereto.

13. The pipe inspection tool of claim 8, wherein the transmitter is a first transmitter, further comprising a second transmitter nearly identical to the first transmitter on the pipe inspection tool, the first transmitter being adjacent to the at least one main receiver and the second transmitter being adjacent to the at least one second receiver, each one of the at least one main receiver being nearly identical to one of the at least one second receiver.

14. A non-transitory computer-readable medium storing computer-readable instructions for inspecting a pipe in a well using an eddy-current based pipe inspection tool, the pipe inspection tool having a transmitter, at least one main receiver, and at least one second receiver mounted on the pipe inspection tool, the computer-readable instructions causing a computing system to:
   obtain a first voltage measurement from the at least one main receiver taken at an axial position along the pipe, the first voltage measurement comprising a residual voltage induced in the at least one main receiver by a residual magnetic field resulting from residual magnetism in the pipe;
   obtain a second voltage measurement from the at least one second receiver taken at said axial position along the pipe;
   process the first voltage measurement and the second voltage measurement to obtain a processed measurement representing a difference between the first and second voltage measurements, the processed measurement being substantially free of the residual voltage; and
   estimate a thickness of the pipe using the processed measurement.

15. The computer-readable medium of claim 14, wherein the at least one second receiver comprises an isolated receiver located sufficiently far on the pipe inspection tool from the transmitter so that the isolated receiver has a negligible response to the primary magnetic field or the secondary magnetic field, further comprising computer-readable instructions for causing the computing system to model the effect of the residual magnetic field as a voltage induced by magnetic dipoles along the pipe, determine a field strength of the magnetic dipoles along the pipe, and calculate the residual voltage at the axial position using the field strength of the magnetic dipoles at the axial position.

16. The computer-readable medium of claim 14, wherein the at least one second receiver comprises a nearly identical receiver to each one of the at least one main receiver, each one of the at least one main receiver and the nearly identical receiver corresponding thereto forming a pair of receivers, each of the at least one second receivers being located sufficiently far on the pipe inspection tool from the transmitter so that the at least one second receivers have a negligible response to the primary magnetic field or the secondary magnetic field, further comprising computer-readable instructions for causing the computing system to multiply the second voltage measurement by a ratio of a velocity of the at least one main receiver over a velocity of the at least one second receiver at the axial position and subtract the result from the first voltage measurement.

17. The computer-readable medium of claim 14, wherein the at least one second receiver comprises a nearly identical receiver to each one of the at least one main receiver, each one of the at least one main receiver and the nearly identical receiver corresponding thereto forming a pair of receivers, each main receiver in each pair of receivers being located on the same side of the transmitter as the nearly identical receiver corresponding thereto, further comprising computer-readable instructions for causing the computing system to multiply the second voltage measurement by a ratio of a velocity of the at least one main receiver over a velocity of the at least one second receiver at the axial position and subtract the result from the first voltage measurement.

18. The computer-readable medium of claim 14, wherein the at least one second receiver comprises a nearly identical receiver to each one of the at least one main receiver, each one of the at least one main receiver and the nearly identical receiver corresponding thereto forming a pair of receivers, each main receiver in each pair of receivers being located equidistance from and on opposite sides of the transmitter from the nearly identical receiver corresponding thereto, further comprising computer-readable instructions for causing the computing system to multiply the second voltage measurement by a ratio of a velocity of the at least one main receiver over a velocity of the at least one second receiver at the axial position and subtract the result from the first voltage measurement.

19. The computer-readable medium of claim 14, wherein the transmitter is a first transmitter, further comprising a second transmitter nearly identical to the first transmitter on the pipe inspection tool, the first transmitter being adjacent to the at least one main receiver and the second transmitter being adjacent to the at least one second receiver, each one of the at least one main receiver being nearly identical to one of the at least one second receiver, further comprising computer-readable instructions for causing the computing system to multiply the second voltage measurement by a ratio of a velocity of the at least one main receiver over a velocity of the at least one second receiver at the axial position and subtract the result from the first voltage measurement.

20. The computer-readable medium of claim 14, wherein the first voltage measurement further comprises a main voltage induced in the main receiver by a primary magnetic field generated by the transmitter and a secondary magnetic field resulting from eddy currents in the pipe.

* * * * *